(12) United States Patent
Hirsh et al.

(10) Patent No.: US 8,758,813 B2
(45) Date of Patent: Jun. 24, 2014

(54) ABUSE-DETERRENT DRUG FORMULATIONS

(71) Applicant: Collegium Pharmaceutical, Inc., Canton, MA (US)

(72) Inventors: Jane Hirsh, Wellesley, MA (US); Alison Fleming, Mansfield, MA (US); Roman Rariy, Philadelphia, PA (US); Alexander M. Klibanov, Boston, MA (US)

(73) Assignee: Collegium Pharmaceutical, Inc., Canton, MA (US)

( * ) Notice: Subject to any disclaimer, the term of this patent is extended or adjusted under 35 U.S.C. 154(b) by 0 days.

(21) Appl. No.: 13/870,690

(22) Filed: Apr. 25, 2013

(65) Prior Publication Data

US 2013/0310413 A1 Nov. 21, 2013

Related U.S. Application Data

(63) Continuation of application No. 12/823,628, filed on Jun. 25, 2010, now Pat. No. 8,449,909, which is a continuation of application No. 11/149,867, filed on Jun. 10, 2005, now Pat. No. 7,771,707.

(60) Provisional application No. 60/579,191, filed on Jun. 12, 2004.

(51) Int. Cl.
*A61K 9/54* (2006.01)
*A61K 9/42* (2006.01)
*A61K 31/44* (2006.01)

(52) U.S. Cl.
USPC .......................... 424/458; 424/476; 514/282

(58) Field of Classification Search
USPC .................................. 424/458, 476; 514/282
See application file for complete search history.

(56) References Cited

U.S. PATENT DOCUMENTS

| | | | |
|---|---|---|---|
| 3,015,128 A | 1/1962 | Somerville, Jr. |
| 3,336,200 A | 8/1967 | Krause et al. |
| 3,773,955 A | 11/1973 | Pachter et al. |
| 3,966,940 A | 6/1976 | Pachter et al. |
| 3,980,766 A | 9/1976 | Shaw et al. |
| 4,070,494 A | 1/1978 | Hoffmeister et al. |
| 4,457,933 A | 7/1984 | Gordon et al. |
| 4,569,937 A | 2/1986 | Baker et al. |
| 4,675,140 A | 6/1987 | Sparks et al. |
| 4,722,941 A | 2/1988 | Eckert et al. |
| 4,861,598 A | 8/1989 | Oshlack |
| 4,869,904 A | 9/1989 | Uekama et al. |
| 5,190,947 A | 3/1993 | Riess et al. |
| 5,356,467 A | 10/1994 | Oshlack et al. |
| 5,460,826 A | 10/1995 | Merrill et al. |
| 5,508,042 A | 4/1996 | Oshlack et al. |
| 5,756,483 A | 5/1998 | Merkus |
| 5,849,240 A | 12/1998 | Miller et al. |
| 5,891,471 A | 4/1999 | Miller et al. |
| 5,914,129 A | 6/1999 | Mauskop |
| 5,952,005 A | 9/1999 | Olsson et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 6,048,736 A | 4/2000 | Kosak |
| 6,068,855 A | 5/2000 | Leslie et al. |
| 6,103,261 A | 8/2000 | Chasin et al. |
| 6,156,764 A | 12/2000 | Asmussen et al. |
| 6,162,467 A | 12/2000 | Miller et al. |
| 6,255,502 B1 | 7/2001 | Penkler et al. |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,309,668 B1 | 10/2001 | Bastin et al. |
| 6,310,072 B1 | 10/2001 | Smith et al. |
| 6,328,979 B1 | 12/2001 | Yamashita et al. |
| 6,335,033 B2 | 1/2002 | Oshlack et al. |
| 6,375,957 B1 | 4/2002 | Kaiko et al. |
| 6,379,707 B2 | 4/2002 | Vladyka, Jr. et al. |
| 6,475,494 B2 | 11/2002 | Kaiko et al. |

(Continued)

FOREIGN PATENT DOCUMENTS

| EP | 0253104 A1 | 1/1988 |
|---|---|---|
| EP | 0375063 A1 | 6/1990 |

(Continued)

OTHER PUBLICATIONS

"Castor oil, hydrogenated," European Pharmacopoeia V.5, p. 1197-1198 (2005).

(Continued)

*Primary Examiner* — Renee Claytor

(74) *Attorney, Agent, or Firm* — Cooley LLP

(57) ABSTRACT

An abuse-deterrent pharmaceutical composition has been developed to reduce the likelihood of improper administration of drugs, especially drugs such as opioids. In one embodiment, the drug is modified to increase its lipophilicity by forming a salt between the drug and one or more fatty acids wherein the concentration of the one or more fatty acids is one to 15 times the molar amount of the active agent. The abuse-deterrent composition prevents the immediate release of a substantial portion of drug, even if the physical integrity of the formulation is compromised and the resulting material is placed in water, snorted, or swallowed. However, when administered as directed, the drug is slowly released from the composition as the composition is broken down or dissolved gradually within the GI tract by a combination of enzymatic degradation, surfactant action of bile acids, and mechanical erosion.

20 Claims, 2 Drawing Sheets

(56) References Cited

U.S. PATENT DOCUMENTS

| | | |
|---|---|---|
| 6,692,767 B2 | 2/2004 | Burnside et al. |
| 6,696,088 B2 | 2/2004 | Oshlack et al. |
| 6,706,281 B2 | 3/2004 | Oshlack et al. |
| 6,723,343 B2 | 4/2004 | Kugelmann |
| 6,743,442 B2 | 6/2004 | Oshlack et al. |
| 6,919,372 B1 | 7/2005 | Yamashita et al. |
| 7,011,846 B2 | 3/2006 | Shojaei et al. |
| 7,261,529 B2 | 8/2007 | Persyn et al. |
| 7,399,488 B2 | 7/2008 | Hirsh et al. |
| 7,670,612 B2 | 3/2010 | Miller |
| 7,771,707 B2 | 8/2010 | Hirsh et al. |
| 8,449,909 B2 | 5/2013 | Hirsh et al. |
| 2001/0006650 A1 | 7/2001 | Burnside et al. |
| 2001/0036476 A1 | 11/2001 | Oshlack et al. |
| 2002/0032166 A1 | 3/2002 | Shefter et al. |
| 2002/0081333 A1 | 6/2002 | Oshlack et al. |
| 2003/0059397 A1 | 3/2003 | Hughes |
| 2003/0064099 A1 | 4/2003 | Oshlack et al. |
| 2004/0052731 A1 | 3/2004 | Hirsh et al. |
| 2004/0062778 A1 | 4/2004 | Shefer et al. |
| 2005/0013862 A1 | 1/2005 | Tobyn et al. |
| 2005/0181050 A1 | 8/2005 | Hirsh et al. |
| 2005/0281748 A1 | 12/2005 | Hirsh et al. |
| 2006/0104909 A1 | 5/2006 | Vaghefi et al. |
| 2008/0199530 A1 | 8/2008 | Hirsh et al. |
| 2008/0260819 A1 | 10/2008 | Fleming et al. |
| 2009/0297617 A1 | 12/2009 | Rariy et al. |
| 2010/0260834 A1 | 10/2010 | Hirsh et al. |
| 2011/0142943 A1 | 6/2011 | Rariy et al. |
| 2013/0045960 A1 | 2/2013 | Hirsh et al. |

FOREIGN PATENT DOCUMENTS

| | | |
|---|---|---|
| EP | 0578231 A1 | 1/1994 |
| EP | 0647448 A1 | 4/1995 |
| GB | 1513166 | 6/1978 |
| WO | WO 93/10765 A1 | 6/1993 |
| WO | WO 95/20947 A1 | 8/1995 |
| WO | WO 97/14438 A1 | 4/1997 |
| WO | WO 97/49402 A1 | 12/1997 |
| WO | WO 98/18827 A1 | 5/1998 |
| WO | WO 00/50007 A1 | 8/2000 |
| WO | WO 01/08661 A2 | 2/2001 |
| WO | WO 01/58447 A1 | 8/2001 |
| WO | WO 01/72338 A1 | 10/2001 |
| WO | WO 03/004029 A1 | 1/2003 |
| WO | WO 2004/075877 A1 | 9/2004 |

OTHER PUBLICATIONS

"International Preliminary Report on Patentability," 3 pages, PCT appl. No. PCT/US03/21095 (Apr. 25, 2005).

"International Preliminary Report on Patentability," 6 pages, PCT appl. No. PCT/US2005/020588 (Oct. 2, 2006).

"International Search Report," 2 pages, PCT appl. No. PCT/US03/21095 (Nov. 6, 2003).

"International Search Report," 4 pages, PCT appl. No. PCT/US2005/020588 (Sep. 9, 2005).

"Supplementary European Search Report," 7 pages, EP appl. No. 03763229.6 (Sep. 19, 2008).

"Written Opinion of the International Searching Authority," 6 pages, PCT appl. No. PCT/US2005/020588 (Sep. 9, 2005).

"Written Opinion," 4 pages, PCT appl. No. PCT/US03/21095 (Jun. 20, 2004).

Abuse and Mental Health Services Administration, "Results from the 2004 National Survey on Drug Use and Health: National Findings," pp. 1-310 (2005).

Bush et al., "A comparison of a theophylline-ephedrine combination with terbutaline," Ann. Allergy 41:13-17 (1978) abstract.

Chemical Abstract Society (CAS), Properties for HPMC (CAS reg. No. 9004-65-3) accessed Jun. 29, 2013.

Choi et al., "Hydrophobic ion pair formation between leuprolide and sodium oleate for sustained release from biodegradable polymeric microspheres," Int. J. Pharm. 203:193-202 (2000).

Cortesi, et al., "Sugar cross-linked gelatin for controlled release: microspheres and disks," Biomaterials 19:1641-1649 (1998).

Gennaro, ed., Remington: The Science and Practice of Pharmacology, $20^{th}$ ed., Lipincott: Baltimore, MD, pp. 704-706 (2000).

Lan et al., "Studies on the Synthesis and Thermal Properties of Copoly(L-lactic acid/glycolic acid) by Direct Melt Polycondensation," J. Appl. Polymer Sci. 92:2163-2168 (2004).

Nakmura, et al., "Development of an oral sustained release drug delivery system utilizing pH-dependent swelling of carboxyvinyl polymer", J. Control. Rel., 111:309-319 (2006).

Raffin et al., "Sodium pantoprazole-loaded enteric microparticles prepared by spray drying: Effect of the scale of production and process validation," Int. J. Pharm. 324:10-18 (2006).

Redden et al., "In vitro hydrolysis of polyunsaturated fatty acid N-acyloxymethyl derivatives of theophylline," Int. J. Pharm. 165:87-96 (1998).

Rodriguez et al., "Description and preliminary evaluation of a new ultrasonic atomizer for spray-congealing processes," Int. J. Pharm. 183(2):133-143 (1999).

Takka et al., "Effect of anionic polymers on the release of propanol hydrochloride from matrix tablets," Eur. J. Pharm. Biopharm. 52:75-82 (2001).

U.S. Appl. No. 14/054,513, filed Oct. 15, 2013.

ABUSE-DETERRENT DRUG FORMULATIONS

CROSS-REFERENCE TO RELATED APPLICATIONS

This application is a continuation of pending prior application U.S. Ser. No. 12/823,628 filed Jun. 25, 2010, entitled "Abuse-Deterrent Drug Formulations" by Jane Hirsh, Alison B. Fleming, Roman V. Ran and Alexander M. Klibanov which is a continuation of pending prior application U.S. Ser. No. 11/149,867 filed Jun. 10, 2008, entitled "Abuse-Deterrent Drug Formulations" by Jane Hirsh, Alison B. Fleming, Roman V. Rariy, and Alexander M. Klibanov, and claims priority under 35 U.S.C. §119 to U.S. Provisional Patent Application No. 60/579,191 filed Jun. 12, 2004 entitled "Abuse-Deterrent Drug Formulations," all of which are hereby incorporated by reference in their entireties and for all purposes.

FIELD OF THE INVENTION

The present invention is generally in the field of pharmaceutical compositions, specifically compositions designed to reduce the potential for improper administration of drugs that are subject to abuse.

BACKGROUND OF THE INVENTION

Oxycodone, morphine, and other opioid analgesics are therapeutically useful and effective medications, e.g., as pain killers, when administered orally. Unfortunately, they also pose a severe threat for willful abuse due to their ability to alter mood and/or cause a sense of euphoria. Currently available sustained release formulations of such drugs, which contain a relatively large amount of drug intended to be released from the formulation over an extended period of time, are particularly attractive to abusers since the sustained release coating can be destroyed by crushing or grinding the formulation. The crushed material no longer controls the release of drug. Depending on the drug, abusers can then (1) snort the material, (2) swallow the material or (3) dissolve the material in water and subsequently inject it intravenously. The dose of drug contained in the formulation is thus absorbed immediately through the nasal or GI mucosa (for snorting or swallowing, respectively) or is administered systemically in a bolus via the circulatory system (for IV injection). These abuse methods result in the rapid bioavailability of relatively high doses of drug, giving the abuser a "high". Since relatively simple methods (crushing, grinding, chewing and/or dissolution in water) can be used to transform such formulations into an abusable form, they provide virtually no deterrent to a potential abuser.

For example, the FDA recently strengthened the warnings and precautions sections in the labeling of OxyContin® (oxycodone HCl controlled-release) tablets, a narcotic drug approved for the treatment of moderate to severe pain, because of continuing reports of abuse and diversion. OxyContin® contains oxycodone HCl (available in 10, 20, 40 and 80 mg strengths), an opioid agonist with an addiction potential similar to that of morphine. Opioid agonists are substances that act by attaching to specific proteins called opioid receptors, which are found in the brain, spinal cord, and gastrointestinal tract. When these drugs attach to certain opioid receptors in the brain and spinal cord they can effectively block the transmission of pain messages to the brain. OxyContin® is supplied in a controlled-release dosage form and is intended to provide up to 12 hours of relief from moderate to severe pain. The warning specifically states that the tablet must be taken whole and only by mouth. When the tablet is chewed or crushed and its contents are swallowed, snorted into the nostrils or dissolved and subsequently injected intravenously, the controlled release mechanism is destroyed and a potentially lethal dose of oxycodone becomes bioavailable.

In recent years, there have been numerous reports of Oxycodone diversion and abuse in several states. For example, DEA's Office of Diversion Control reported 700 OxyContin® thefts in the U.S. between January 2000 and June 2001. Some of these reported cases have been associated with serious consequences including death.

Oxycodone is a controlled substance in Schedule II of the Controlled Substances Act (CSA), which is administered by the Drug Enforcement Administration (DEA). Despite the fact that Schedule II provides the maximum amount of control possible under the CSA for approved drug products, in practice, it is difficult for law enforcement agencies to control the diversion or misuse of legitimate prescriptions. Although abuse, misuse, and diversion are potential problems for all opioids, including Oxycodone, opioids are a very important part of the medical arsenal for the management of pain when used appropriately under the careful supervision of a physician.

Currently available formulations for such drugs are designed for oral administration but do not include mechanisms to prevent or retard improper methods of administration such as chewing, injection and snorting. This represents a serious problem given the large number of legitimate prescriptions written in the U.S.; for example, the medical use of opioids within the U.S. increased 400% from 1996 to 2000. The problems with abuse are significant and longstanding, and efforts to design new abuse-resistant or abuse-deterrent formulations have been largely unsuccessful. U.S. Pat. Nos. 3,980,766, 4,070,494 and 6,309,668 describe formulations designed to prevent the injection of compositions meant for oral administration. U.S. Pat. No. 3,980,766 describes the incorporation of an ingestible solid which causes a rapid increase in viscosity upon concentration of an aqueous solution thereof. U.S. Pat. No. 4,070,494 describes the incorporation of a non-toxic, water gelable material in an amount sufficient to render the drug resistant to aqueous extraction. U.S. Pat. No. 6,309,668 describes a tablet for oral administration containing two or more layers comprising one or more drugs and one or more gelling agents within separate layers of the tablet. The resulting tablet forms a gel when combined with the volume of water necessary to dissolve the drug; this formulation thus reduces the extractability of the drug from the tablet. It should be noted that although these compositions preclude abuse by injection, this approach fails to prevent abuse by crushing and swallowing or snorting the formulation, which are commonly reported methods of abuse associated with OxyContin®.

U.S. Pat. Nos. 3,773,955 and 3,966,940 describe formulations containing a combination of opioid agonists and antagonists, in which the antagonist does not block the therapeutic effect when the admixture is administered orally, but which does not produce analgesia, euphoria or physical dependence when administered parenterally by an abuser. U.S. Pat. No. 4,457,933 describes a method for decreasing both the oral and parenteral abuse potential of strong analgesic agents by combining an analgesic dose of the analgesic agent with an antagonist in specific, relatively narrow ratios. U.S. Pat. Nos. 6,277,384, 6,375,957 and 6,475,494 describe oral dosage forms including a combination of an orally active opioid agonist and an orally active opioid antagonist in a ratio that, when delivered orally, is analgesically effective but that is aversive in a physically dependent subject. While such a formulation may be successful in deterring abuse, it also has the potential to produce adverse effects in legitimate patients.

It is therefore an object of the present invention to provide a pharmaceutical composition that significantly reduces the potential for improper administration or use of drugs but which, when administered as directed, is capable of delivering a therapeutically effective dose.

BRIEF SUMMARY OF THE INVENTION

An abuse-deterrent pharmaceutical composition has been developed to reduce the likelihood of improper administration of drugs, especially drugs such as opioids. In the preferred embodiment, the drug is modified to increase its lipophilicity by forming a salt between the drug and one or more fatty acids or amines, wherein the concentration of the one or more fatty acids or amines is one to fifteen times the molar amount of the active agent, preferably two to ten times the molar amount of the active agent. In one embodiment the modified drug is homogeneously dispersed within microparticles composed of a material that is either slowly soluble or insoluble in water. In some embodiments the drug containing microparticles or drug particles are coated with one or more coating layers. The abuse-deterrent composition prevents the immediate release of a substantial portion of drug, even if the physical integrity of the formulation is compromised (for example, by chopping with a blade or crushing) and the resulting material is placed in water, snorted, or swallowed. However, when administered as directed, the drug is slowly released from the composition as the composition is broken down or dissolved gradually within the GI tract by a combination of enzymatic degradation, surfactant action of bile acids, and mechanical erosion.

DETAILED DESCRIPTION OF THE INVENTION

I. Definitions

Figure 1:
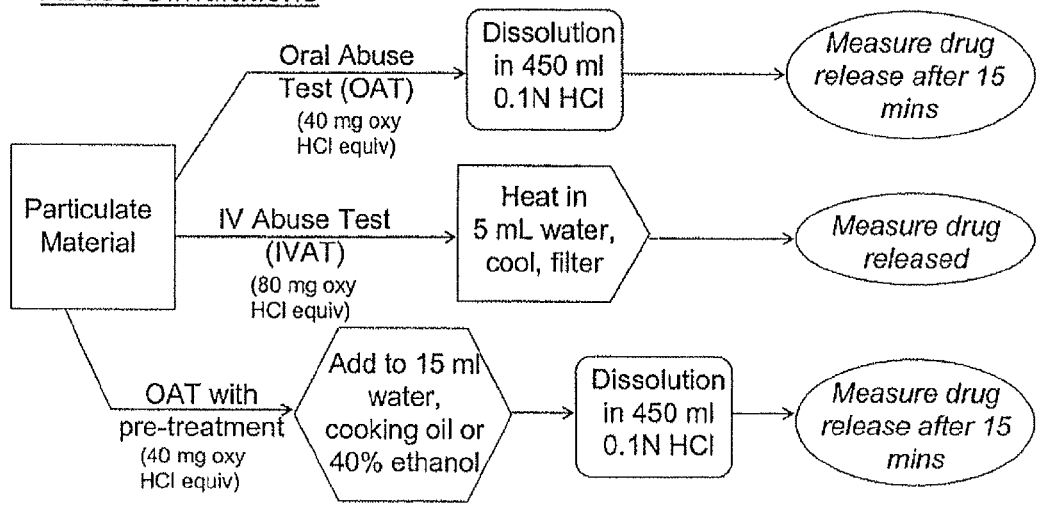
FIG. 1 is an illustration of the testing procedures for determining abuse resistance of the formulations.

"Composition" as used herein refers to the drug dosage unit for administration to a patient. It may also be used in reference solely to the active ingredient, or to the formulation containing the active ingredient.

"Abuse-deterrent composition" or "abuse-deterrent formulation" are used interchangeably herein to refer to compositions that reduce the potential for improper administration of drugs but that deliver a therapeutically effective dose when administered as directed. Improper administration includes tampering with the dosage form and/or administering the drug by any route other than instructed.

"Drug", "active agent", and "pharmacologically active agent" are used interchangeably herein to refer to a chemical compound that induces a desired pharmacological and/or physiological effect. The terms also encompass pharmaceutically acceptable derivatives of those active agents specifically mentioned herein, including, but not limited to, salts, solvates, hydrates, complexes with one or more molecules, prodrugs, active metabolites, lipophilic derivatives, analogs, and the like.

"Lipophilic derivative" and "lipophililic drug derivative", as used herein, refer to derivatives of the drug that are less soluble in water than the most soluble salt of the drug. The most soluble salt is selected from either alkaline metal salts (for acidic drugs) or acid addition salts of (for basic drugs).

"Microparticle" as used herein refers to a composition comprising a drug dispersed within a carrier material. "Coated microparticle" as used herein refers to a composition comprising a drug containing microparticle or a drug particle coated with one or more coating layers. Microparticles and coated microparticles have a size range of 10 to 3000 microns in diameter.

II. Compositions

The currently available sustained release dosage forms containing narcotic analgesics and other drugs are subject to misuse, in part, because mechanical destruction of the dosage form exposes the encapsulated drug and allows for immediate dissolution of the drug into aqueous media. Two properties of the dosage form that contribute to this outcome are (1) the ease with which drug is exposed to the extraction media and (2) the high water solubility of the drug salt form.

In the composition disclosed herein, one or both of these properties are altered in order to achieve an abuse-deterrent composition. Specifically, in the preferred embodiment, the drug is modified to increase its lipophilicity and, in additional preferred embodiments, is then homogeneously dispersed within a material that is either slowly soluble or not soluble in water and subsequently formulated into microparticles. The drug may be present in the form of discrete particles or may be partially or fully dispersed in the carrier material on a molecular level.

The abuse deterrent composition preferably comprises a drug modified to increase its lipophilicity. In other preferred embodiments, the drug is homogenously dispersed within microparticles composed of a material that is either slowly soluble in water or water insoluble. The compositions slow the release of drug if the dosage form is chopped or crushed and the resulting material is placed in water, snorted, or swallowed since most of the drug will remain associated with or entrapped within portions of the core material of the microparticles. In some embodiments the drug containing microparticles or individual drug particles are coated with one or more coating layers, where at least one coating is water insoluble and preferably organic solvent insoluble, but enzymatically degradable. The components of the resulting coated microparticles are not mutually soluble in water, organic solvents, or any combination thereof, such that no one solvent or enzyme solution is capable of dissolving the formulation in its entirety in vitro. It follows that extraction of the drug from the formulation cannot be carried out in one step. However, when administered as directed, the drug is slowly released from the formulation since it is eroded within the environment of the gastrointestinal tract.

A. Drugs to be Formulated

There are many drugs that it is desirable to deliver using the compositions described herein. The Controlled Substances Act (CSA), Title II of the Comprehensive Drug Abuse Prevention and Control Act of 1970, places all substances that are regulated under existing federal law into one of five schedules based upon the substance's medicinal value, harmfulness, and potential for abuse or addiction. Drugs that are preferred include those classified as Schedule II, III, IV and V drugs. Drugs that are most preferable include those, like oxycodone, that are currently formulated as sustained or controlled release compositions, where drug release is intended to occur over a prolonged period of time through the gastrointestinal tract, and immediate or burst release, for example, by inhalation or injection, is undesirable. As used herein, drugs prone to abuse refer to controlled substance specified as schedule II, II, IV and V drugs.

The terms "drug", "active agent", and "pharmacologically active agent" are used interchangeably herein to refer to a chemical compound that induces a desired pharmacological, physiological effect. The terms also encompass pharmaceutically acceptable derivatives of those active agents specifically mentioned herein, including, but not limited to, salts, solvates, hydrates, complexes with one or more molecules, prodrugs, active metabolites, lipophilic derivatives, analogs, and the like. When the terms "active agent", "pharmacologically active agent" and "drug" are used, or when a particular drug, such as oxycodone, is identified, it is to be understood as including the active agent per se as well as pharmaceutically acceptable salts, solvates, hydrates, complexes with one or more molecules, prodrugs, active metabolites, and lipophilic derivatives and analogs.

Examples of preferred drugs include, 1-phenylcyclohexylamine, 1-piperidinocyclohexanecarbonitrile, alfentanil, alphacetylmethadol, alphaprodine, alprazolam, amobarbital, amphetamine, anileridine, apomorphine, aprobarbital, barbital, barbituric acid derivative, bemidone, benzoylecgonine, benzphetamine, betacetylmethadol, betaprodine, bezitramide, bromazepam, buprenorphine, butabarbital, butalbital, butorphanol, camazepam, cathine, chloral, chlordiazepoxide, clobazam, clonazepam, clorazepate, clotiazepam, cloxazolam, cocaine, codeine, chlorphentermine, delorazepam, dexfenfluramine, dextromoramide, dextropropoxyphen, dezocine, diazepam, diethylpropion, difenoxin, dihydrocodeine, dihydromorphine, dioxaphentyl butyrate, dipanone, diphenoxylate, diprenorphine, ecgonine, enadoline, eptazocine, estazolam, ethoheptazine, ethyl loflazepate, ethylmorphine, etorphine, femproponex, fencamfamin, fenfluramine, fentanyl, fludiazepam, flunitrazepam, flurazepam, glutethimide, halazepam, haloxazolam, hexalgon, hydrocodone, hydromorphone, isomethadone, hydrocodone, ketamine, ketazolam, ketobemidone, levanone, levoalphacetylmethadol, levomethadone, levomethadyl acetate, levomethorphan, levorphanol, lofentanil, loperamide, loprazolam, lorazepam, lormetazepam, lysergic acid, lysergic acid amide, mazindol, medazepam, mefenorex, meperidine, meptazinol, metazocine, methadone, methamphetamine, methohexital, methotrimeprazine, methyldihydromorphinone, methylphenidate, methylphenobarbital, metopon, morphine, nabilone, nalbuphine, nalbupine, nalorphine, narceine, nefopam, nicomorphine, nimetazepam, nitrazepam, nordiazepam, normethadone, normorphine, oxazepam, oxazolam, oxycodone, oxymorphone, pentazocine, pentobarbital, phenadoxone, phenazocine, phencyclidine, phendimetrazine, phenmetrazine, pheneridine, piminodine, prodilidine, properidine, propoxyphene, racemethorphan, racemorphan, racemoramide, remifentanil, secobarbital, sufentanil, talbutal, thebaine, thiamylal, thiopental, tramadol, trimeperidine, and vinbarbital.

In addition to the compounds above, the following scheduled drugs may be incorporated into the composition: allobarbitone, alprazolam, amylobarbitone, aprobarbital, barbital, barbitone, benzphetamine, brallobarbital, bromazepam, brotizolam, buspirone, butalbital, butobarbitone, butorphanol, camazepam, captodiame, carbromal, carfentanil, carpipramine, cathine, chloral, chloral betaine, chloral hydrate, chloralose, chlordiazepoxide, chlorhexadol, chlormethiazole edisylate, chlormezanone, cinolazepam, clobazam, potassium clorazepate, clotiazepam, cloxazolam, cyclobarbitone, delorazepam, dexfenfluramine, diazepam, diethylpropion, difebarbamate, difenoxin, enciprazine, estazolam, ethyl loflazepate, etizolam, febarbamate, fencamfamin, fenfluramine, fenproporex, fluanisone, fludiazepam, flunitraam, flunitrazepam, flurazepam, flutoprazepam, gepirone, glutethimide, halazepam, haloxazolam, hexobarbitone, ibomal, ipsapirone, ketazolam, loprazolam mesylate, lorazepam, lormetazepam, mazindol, mebutamate, medazepam, mefenorex, mephobarbital, meprobamate, metaclazepam, methaqualone, methohexital, methylpentynol, methylphenobarbital, midazolam, midazolam, morphine, nimetazepam, nitrazepam, nordiazeparn, oxazepam, oxazolam, paraldehyde, pemoline, pentabarbitone, pentazocine, pentobarbital, phencyclidine, phenobarbital, phendimetrazine, phenmetrazine, phenprobamate, phentermine, phenyacetone, pinazepam, pipradol, prazepam, proxibaxbal, quazepam, quinalbaritone, secobarbital, secbutobarbitone, sibutramine, temazepam, tetrazepam, triazolam, triclofos, zalepan, zaleplon, zolazepam, zolpidem, and zopiclone. In a preferred embodiment, the pharmaceutically active agent is oxycodone.

Certain compounds described herein may exist in particular geometric or stereoisomeric forms. The compositions disclosed herein contemplate all such compounds, including cis- and trans-isomers, R- and S-enantiomers, diastereomers, (D)-isomers, (O-isomers, the racemic mixtures thereof, compounds of different spatial conformations, and other mixtures thereof Additional asymmetric carbon atoms may be present in a substituent such as an alkyl group.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704, the disclosure of which is hereby incorporated by reference.

Optionally, the composition described herein can further include a drug having no appreciable abuse potential.

In preferred embodiments, the solubility characteristics of a drug are altered prior to incorporation into the formulation. Modification of the drug to produce a more lipophilic derivative serves to reduce the water solubility of the drug and thus reduces the aqueous extractability. Furthermore, if the drug is made more lipophilic, it can be solubilized in a fatty substance or wax like mixture, rather than physically dispersed in a particulate form. Solubilization of drug enhances the abuse-deterrent properties of microparticles formulated from the mixture as it is difficult to extract drug from an intimately dispersed composition.

Some of the methods that can be used to alter the drug's lipophilicity are outlined below. It is understood that two or more approaches can be combined to achieve a desired solubility profile.

B. Lipophilic Drug Formulations

In one embodiment, drug is made more lipophilic by eliminating or reducing the overall charge of the drug molecule. For example, for a basic drug, a water soluble salt (such as hydrochloride, sulfate, or maleate) can be converted to a free base using techniques known in the art. Correspondingly, in the case of an acidic drug, a water soluble salt (such sodium, potassium, or the like) can be converted to a free acid.

In another embodiment, the drug's lipophilicity is increased by forming a salt between a drug molecule and one or more charged lipophilic compounds. In this case the lipophilicity of the resulting salt can be manipulated by varying the lipophilicity of the counter-ion. In general lipophilic (fatty) acids or amines with chain lengths between $C_5$-$C_{30}$ are suitable lipophilic counter-ion candidates. Suitable (fatty) acids and amines include, but are not limited to, pentanoic acid, hexanoic (caproic) acid, heptanoic acid, octanoic (caprylic) acid, nonanoic acid, decanoic (capric) acid, undecanoic acid, dodecanoic (lauric) acid, tridecanoic acid, tetradecanoic (myristic) acid, pentadecanoic acid, hexadecanoic (palmitic) acid, heptadecanoic (margaric) acid, octadecanoic (stearic) acid, nonadecanoic acid, eicosanoic (arachidic) acid, heneicosanoic acid, docosanoic (behenic) acid, tricosanoic acid, tetracosanoic (lignoceric) acid, pentacosanoic acid, hexacosanoic acid, heptacosanoic acid, octacosanoic acid, nonacosanoic acid, triacontanoic acid, linoleic acid, oleic acid, octyl amine, lauryl amine, stearyl amine, palmityl amine, linoleyl amine, and oleyl amine and mixtures thereof. In a preferred embodiment, the fatty acid is myristic acid or a mixture of stearic and palmitic acid. The fatty acid or amine is present in an amount from about one to about fifteen times the molar amount of the pharmaceutically active agent, preferably two to ten times the molar of amount of the pharmaceutically acceptable agent.

The formation of a salt composed of a pharmaceutically active agent and a fatty acid or amine can be accomplished by a melt process, with or without the use of a solvent. One or more fatty acids or amines are heated above their melting point and the pharmaceutically active agent, in free base or acid form, is added to the molten fatty acid or amine either directly or after dissolution of the active agent in an appropriate solvent, such as methylene chloride. The lipophilic compound is present in excess (on a molar basis) relative to the pharmaceutically active agent. The lipophilic compound is present, preferably, in an amount one to fifteen times the molar amount of the pharmaceutically active agent, more preferably, two to ten times the molar amount of the pharmaceutically active agent. The mass of fatty acid or amine required to dissolve the active agent is a function of the chain length of the fatty acid or amine. For example, oxycodone base can be dissolved in a molten mixture of stearic and plamitic acids at a ratio of 1:5, by weight, or in molten myristic acid at a ratio of 1:4, by weight. The factors determining the amount of fatty acid or amine required to dissolve a given amount of base include but are not limited to base strength, acid strength, steric hindrance of the portions of the acid and/or base molecule involved in salt formation, and the ability of the base to form non-ionic interactions (i.e. hydrogen bonds), with the acid molecules.

Other salts which may increase lipophilicity and, hence, lipid solubility relative to the parent drug compound include, but are not limited to, pectinate, tannate, phytate, salicylate, saccharinate, acesulfamate, gallate, and terephthalate salts.

In another embodiment, a drug is covalently modified to increase its lipophilicity. For example, a lipophilic compound can be covalently attached to a drug molecule via an ester or amide linkage. Such drug derivatives are cleaved in vivo, thus releasing the parent compound.

C. Drug Containing Microparticles

In preferred embodiments, drugs are formulated with a carrier material to form microparticles. As used herein, the term "microparticle" refers to a composition comprising a drug dispersed within a carrier material and "coated microparticle" refers to a composition comprising a drug containing microparticle or a drug particle coated with one or more coating layers of material. Microparticles and coated microparticles have a size range of 10 to 3000 microns in diameter.

Within microparticles, drug is preferably homogeneously dispersed in the form of fine particles within the carrier material. More preferably, drug is partially solubilized in molten carrier material or partially dissolved with the carrier material in a mutual solvent during the formulation of the microparticles. Most preferably, drug is completely solubilized in the carrier material or completely dissolved with the carrier material in a co-solvent during the formulation of the microparticles. This is accomplished through the selection of materials and the manner in which they are processed.

Carrier materials appropriate for the fabrication of drug containing microparticles are either slowly soluble in water or insoluble in water, but capable of degrading within the Gi tract by means including enzymatic degradation, surfactant action of bile acids and mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to castor oil, safflower oil, olive oil, canola oil, sunflower oil, vegetable oil, corn oil, hydrogenated vegetable oil, hydrogenated cottonseed oil, hydrogenated castor oil, hydrogenated oils available under the trade name Sterotex®, stearic acid, cocoa butter, and stearyl alcohol. Oils and hydrogenated oils in admixture with one another may also be used as carrier materials. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C. In a preferred embodiment, the carrier is beeswax, carnauba wax or a mixture thereof.

In some cases, it may be desirable to alter the rate of water penetration into the hydrophobic drug containing microparticles. To this end, rate-controlling (wicking) agents may be formulated along with the fats or waxes listed above. Examples of rate-controlling materials include certain starch derivatives (eg, waxy maltodextrin and drum dried corn starch), cellulose derivatives (eg, hydroxypropylmethylcellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins which are water insoluble, such as zein, are preferred carrier materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Certain polymers may also be used as carrier materials in the formulation of drug containing microparticles. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as carrier materials for drug containing microparticles.

Encapsulation or incorporation of drug into carrier materials to produce drug containing microparticles can be achieved through known pharmaceutical formulation techniques. To create a composition that protects drug from exposure upon mechanical disruption (eg, grinding, chewing, or chopping), the drug is intimately dispersed within the carrier material. In the case of formulation in fats, waxes or wax-like materials, the carrier material is heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stifling as the mixture cools. Alternatively, the molten wax-drug mixture can be extruded and spheronized to form pellets or beads. For formulations comprising salts composed of a pharmaceutically active agent and one or more fatty acids or amines, the one or more fatty acids or amines are melted and mixed with the free base or acid form of the active agent at a temperature above the melting point(s) of the fatty acid(s) or amine(s) but below the melting point of the active agent. Once a homogeneous mixture is formed, a carrier material such as a fat, fatty substance, wax or wax-like substance can be added to the molten mixture to yield a single phase composition. The molten solution is solidified and formulated into microparticles. Detailed descriptions of these processes can be found in "Remington—The science and practice of pharmacy", 20$^{th}$ Edition, Jennaro et. Al., (Phila, Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In addition to modification of the drug itself, processing conditions can be used to influence the dispersion of the drug within water-insoluble or slowly water soluble material. For example, in the case where the water in-soluble or slowly soluble material is melted and drug is fully or partially dissolved under stirring conditions, the temperature, agitation rate and time of processing will influence the degree of dissolution achieved. More specifically, a more homogenous dispersion may be achieved with a higher temperature, faster stirring rate and longer processing time. Ultrasound can also be applied to the molten mixture to increase the degree of dispersion and/or the rate of dissolution of the drug.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

D. Coated Drug Containing Microparticles

In some embodiments, drug containing microparticles or drug particles are encapsulated within at least one water-insoluble enzymatically degradable material. In some instances the substrates of digestive enzymes are naturally water-insoluble and can be utilized in the formulation without further processing. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., Biomaterials 19 (1998) 1641-1649). Cross-linking can also be accomplished using enzymatic means; for example, transglutaminase. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions. Insoluble coatings can be formed on particles in this fashion. It should be noted that in many cases polysaccharides are broken down specifically by enzymes produced by bacteria within the colon.

In some cases a water-insoluble but enzymatically degradable coating comprising both a protein and a polysaccharide can be produced if the components are oppositely charged polyelectrolytes. Under the proper temperature, pH, and concentrations, the two polymers can interact through their opposite electrical charges and form a water-insoluble complex. If a core particle is present at the time the complex phase separates, it will be coated. For example, gelatin and gum arabic can be coated onto a core particle utilizing this process. Optionally, the complex can be made irreversibly insoluble by subsequent cross-linking induced by chemical or physical means.

In some embodiments it may be desirable to coat the drug containing microparticles with a non-enzymatically degradable coating. Such coatings generally release drug via diffusion through pores in the coating.

In general, any coating procedure which provides a coating on each particle of drug containing microparticle without significant agglomeration of particles may be used. Coating procedures known in the pharmaceutical art including, but not limited to, fluid bed coating processes, granulation and microencapsulation may be used to obtain appropriate coatings. The coating materials may be any of a large number of natural or synthetic film-formers used singly, in admixture with each other, and in admixture with plasticizers (for example, Durkex 500 vegetable oil), pigments and other substances to alter the characteristics of the coating. In general, the major components of the coating should be insoluble in, and permeable to, water. However, it might be desirable to incorporate a water-soluble substance, such as methyl cellulose, to alter the permeability of the coating. The coating materials may be applied as a suspension in an aqueous fluid or as a solution in organic solvents. The water-permeable diffusion barrier may consist of ethyl cellulose, methyl cellulose and mixtures thereof. The water-permeable diffusion bather may also consist of water insoluble synthetic polymers sold under the trade name Eudragit® (Rohm Pharma), such as Eudragit RS, Eudragit RL, Eudragit NE and mixtures thereof. Other examples of such coating materials can be found in the Handbook of Pharmaceutical Excipients, Ed. By A. Wade and P. J. Weller, (1994), incorporated by reference herein.

As used herein, the term water-permeable is used to indicate that the fluids of the alimentary canal will permeate or penetrate the coating film with or without dissolving the film or parts of the film. Depending on the permeability or solubility of the chosen coating (polymer or polymer mixture) a lighter or heavier application thereof is required to obtain the desired release rate.

E. Dosage Forms

There are a number of drug compositions that meet the abuse deterrent criteria outlined above. In one embodiment a drug is homogeneously dispersed, in a fine particulate form, within a water-insoluble or slowly water soluble material and the mixture is formulated into microparticles. In another embodiment a drug is partially dissolved within a water-insoluble or slowly water soluble material during the manufacturing process, for example, by mixing at a temperature above the melting point of the carrier material, and the mixture is formulated into microparticles. In yet another embodiment a drug is fully dissolved within a water-insoluble or slowly water soluble material during the manufacturing process, for example, by mixing at a temperature above the melting point of the carrier material, and the mixture is formulated into microparticles. In still a further embodiment, the drug containing microparticles, where the drug is homogeneously dispersed in a particulate form, or has been partially or fully dissolved within the carrier material during the manufacturing process, are coated with one or more coatings to form coated microparticles. In a further embodiment, drug particles are coated directly with one or more coatings to form coated microparticles.

The microparticles, coated microparticles, or a mixture thereof are formed into a solid dosage form suitable for oral administration. For example, microparticles or coated microparticles can be incorporated into hard capsules, dispersed within a soft gelatin capsule, or combined with appropriate excipients and tableted by compression. The microparticles, coated microparticles, or a mixture thereof could also be further dispersed in a semisolid hydrophobic material, for example, a mixture of castor oil and hydrogenated castor oil.

In some embodiments, the compositions are coated with an enteric coating. Enteric coatings known in the art are applied directly to the abuse-deterrent microparticle or coated microparticle compositions or are applied to the surface of a capsule or tablet comprising the abuse deterrent microparticle and/or coated microparticle compositions. Enteric coatings known in the art include, for example, acrylic polymers that are commercially available under the trade name EUDRAGIT®, cellulose acetate phthalate, hydroxypropylmethylcellulose phthalate, polyvinylacetate phthalate, shellac, hydroxypropylmethylcellulose succinate, cellulose acetate trimelliate or mixtures thereof.

Dosage forms can include one or more drugs. When the dosage form includes two or more drugs they can be Scheduled drugs or can be a combination of Scheduled and non-Scheduled drugs. The drugs can be incorporated into separate microparticle compositions where the Scheduled drugs are incorporated into abuse deterrent microparticle compositions and the non-Scheduled drugs are incorporated into abuse deterrent microparticle compostions, sustained release compositions known in the art or immediate release compositions known in the art. The compositions comprising the different drugs are formulated into a single solid dosage form suitable for oral administration, for example, they can be incorporated into a gelatin capsule, or combined with appropriate excipients and compressed into a tablet form. Examples of non-scheduled drugs that may be included in dosage forms described herein include, but are not limited to, aspirin, acetaminophen, non-steroidal anti-inflammatory drugs, cyclooxygenase II inhibitors, N-methyl-D-aspartate receptor antagonists, glycine receptor antagonists, triptans, dextromethorphan, promethazine, fiorinal, guaifenesin, butalbital, and caffeine.

An immediate release close can be incorporated into the formulation in several ways. Immediate release microparticles can be made utilizing standard methodologies and formulated along with abuse-deterrent microparticle and/or coated microparticle compositions in a suitable oral dosage form. Alternatively, a coating containing drug which is available for immediate release can be placed on a tablet comprising abuse-deterrent microparticle and/or coated microparticle compositions plus appropriate excipients. Additionally, an immediate dose of drug can be granulated or blended with rapidly dissolving excipients and subsequently compressed (1) as one layer of bi-layer tablets in which the abuse-deterrent microparticle and/or coated microparticle compositions are compressed as the other layer, or (2) as the outer layer of compression-coated tablets in which the abuse-deterrent microparticle and/or coated microparticle compositions are compressed as the inner core, or (3) into tablets in which abuse-deterrent microparticle and/or coated microparticle compositions are embedded.

In some embodiments, the immediate release portion of the dosage form comprises a lipophilic drug derivative. For example, salt derivatives or complexes that are insoluble at a neutral pH but dissociate, thereby releasing the parent compound, at an acidic pH are ideal for immediate release within the stomach. In the case of oxycodone some salts that may exhibit this property include, but are not limited to, the tannate, phthalate, salicylate, gallate, pectinate, phytate, saccharinate, asesulfamate and terephthalate salts. Use of salts in the immediate release portion of the dosage form reduces the abuse potential of the immediate release dose if the formulation is crushed and (1) snorted or (2) dissolved in water since these salts will be poorly soluble under these conditions. It is understood by the one of ordinary skill in the art that such salts may also be used to formulate an immediate release dosage form without a sustained release portion.

Additional mechanisms to reduce the potential for abuse can also be incorporated during the process of formulating tablets. For example, ingredients can be added to deter chewing or snorting of the final formulation. For example, an intensely bitter substance may deter chewing, while an intensely spicy ingredient, such as capsaicin, may deter snorting. The addition of a colored dye, which would stain the skin and mucosal surface of the nose following snorting may also serve to reduce this practice.

Optional excipients present in the oral dosage form comprising abuse deterrent microparticles or coated microparticles include, but are not limited to diluents, binders, lubricants, disintegrants, colorants, plasticizers and the like. Diluents, also termed "fillers," are typically necessary to increase the bulk of a solid dosage form so that a practical size is provided for compression of tablets. Examples of diluents include cellulose, dry starch, microcrystalline cellulose, dicalcium phosphate, calcium sulfate, sodium chloride confectioner's sugar, compressible sugar, dextrates, dextrin, dextrose, sucrose, mannitol, powdered cellulose, sorbitol, and lactose. Binders are used to impart cohesive qualities powdered materials and can include materials such as starch, gelatin, sugars, natural and synthetic gums, polyethylene glycol, ethylcellulose, methylcellulose, hydroxypropylmethylcellulose, carboxymethylcellulose, waxes and polyvinyl pyrrolidone. Lubricants are used to facilitate tablet manufacture; examples of lubricants include talc, magnesium stearate, calcium stearate, hydrogenated vegetable oils stearic acid, sodium stearyl fumarate, sodium benzoate, sodium acetate, leucine, sodium oleate, sodium lauryl sulfate, magnesium lauryl sulfate and polyethylene glycol. Disintegrants can be added to pharmaceutical formulations in order to facilitate "breakup" or disintegration after administration. Materials used for this purpose include starches, clays, celluloses, aligns, gums, and cross-linked polymers. A plasticizer may be included in coating materials to alter their mechanical properties. Examples of plasticizers include benzyl benzoate, chlorobutanol, dibutyl sebacate, diethyl phthalate, glycerin, mineral oil, polyethylene glycol, sorbitol, triacetin, triethyl citrate, glycerol, etc. In addition to the additives above, coloring and flavoring agents may also be incorporated into the composition.

Optionally, the composition disclosed herein comprises materials wherein a combination of the materials is not soluble in water, organic solvent, or any combination thereof.

EXAMPLES

Example 1

Preparation and Testing of Abuse-Resistant Compositions

Compositions comprising oxycodone base, a fatty acid and a third wax component were prepared at several different ratios in the following manner. Oxycodone base (0.2 g) and Butylated Hydroxytoluene (~1 mg) were dissolved in methylene chloride (0.7 ml). The fatty acid(s) and wax(es) were melted together at 95° C. on a heating block until clear solutions were obtained. The oxycodone solution was added to the molten fatty acids/waxes and mixed well. The resulting clear solutions were incubated for 20 minutes to remove the solvent. The mixtures were then solidified and re-melted at 95° C. as an informal test of stability (i.e. to check for base precipitation). Finally, the molten solutions were poured onto sheets of aluminum foil and rapidly cooled to form solid wafers. Note that only formulations that did not show base precipitation were cast into wafers and subjected to further analysis.

The wafer compositions described above were crushed into particles. Sample particles were subjected to the Oral Abuse Test (see FIG. 1 for protocol). Samples were analyzed with a UV spectrophotometer. Results are presented in FIG. 2.

Example 2

Oxycodone with Myristic Acid as a Lipophilic Counter-Ion

Small batches of each microparticle composition were prepared with the following amounts of reagents:

| Oxycodone base/Myristic acid/Beeswax (1:5:2) | |
| --- | --- |
| Ingredient | Amount (g) |
| Oxycodone base | 2.2 g |
| Myristic acid | 11 g |
| Beeswax, NF | 4.4 g |
| BHT | 0.011 g |
| total | 17.611 g |

| Oxycodone base/Myristic Acid/Carnauba wax (1:5:2) | |
| --- | --- |
| Ingredient | Amount (g) |
| Oxycodone base | 2.2 g |
| Myristic acid | 11 g |
| Carnauba wax, NF | 4.4 g |
| BHT | 0.011 g |
| total | 17.611 g |

(1) Myristic acid, Oxycodone base (solid), and BHT were heated to form a homogeneous mixture free of drug crystals. Note that no solvent was used in this stage.
(2) Solid wax was added to the clear solution and allowed to dissolve. The clear mixture was stirred for 5 minutes
(3) The clear solution was poured onto a sheet of aluminum foil and allowed to cool rapidly to form solid wafers The solid wafers produced above were crushed with a mortar and pestle (Oxycodone base/Myristic Acid/Carnauba wax) or cut with a razor blade followed by crushing with a mortar and pestle (Oxycodone base/Myristic Acid/Beeswax). Crushing was carried out with the goal of reducing the particle size to less than 25 mesh. For Oxycodone base/Myristic Acid/Beeswax, crushing was stopped prior to reaching this endpoint due to the difficulty in reducing the particle size of this "gummy" material.

Example 3

Abuse Resistance and Bioavailability Screen

Figure 2:
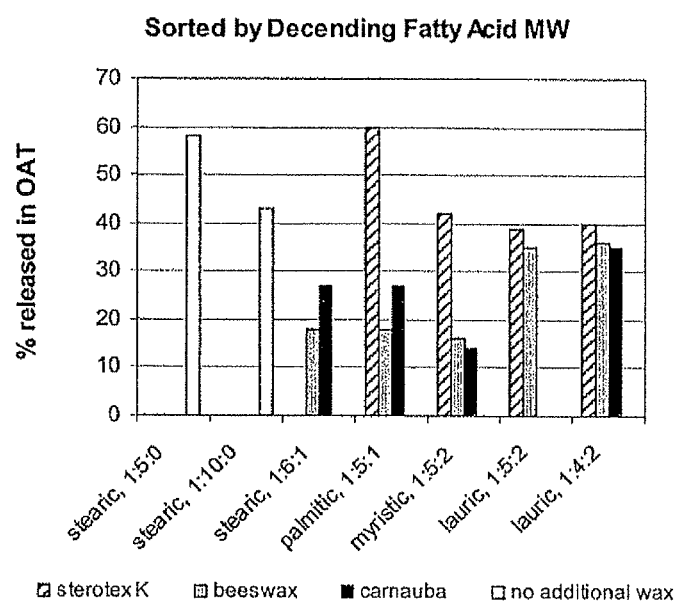
FIG. 2 is a graph showing the percentage of oxycodone released in Oral Abuse Testing as a function of composition.

The microparticles comprising oxycodone base/myristic acid/wax (1:5:2 by weight ratio) described above were subjected to a battery of Abuse Tests and a Bioavailability Screen (see FIG. 1 for protocols). Samples were analyzed via HPLC. The results are shown in Table 1.

TABLE 1

Testing Results for Particles made from oxycodone/myristic acid/wax at a ratio of 1:5:2

| Sample ID | OAT Result (%) | IVAT Result (%) | Bioavail Screen (%) | OAT Water Pre-treat (%) | OAT Oil Pre-treat (%) | OAT Alcohol Pre-treat (%) |
|---|---|---|---|---|---|---|
| Oxycodone Base/Myrisitic acid/carnauba (1:5:2) | 15.2 ± 1.5 | 2.1 ± 0.2 | 107.3 ± 2.4 | 15.9 ± 1.0 | 12.0 ± 0.4 | 27.8 ± 2.3 |
| Oxycodone Base/Myrisitic acid/beeswax (1:5:2) | 17.7 ± 0.7 | 2.4 ± 0.2 | 101.1 ± 0.6 | 24.0 ± 1.3 | 14.6 ± 0.6 | 25.0 ± 1.6 |

Differential Scanning calorimetry was conducted on the samples and on oxycodone base. The results are summarized in Table 2.

TABLE 2

Summary of DSC analysis on Pre-formulations made from oxycodone/myristic acid/wax at a ratio of 1:5:2.

| Sample | Peak Temps (° C.) | Onset of Peaks (° C.) | ΔH (J/g) |
|---|---|---|---|
| Oxycodone Base/Myristic acid/beeswax (1:5:2) | 48.5 | 43.1 | 88.2 |
| Oxycodone Base/Myristic acid/carnauba (1:5:2) | 31.5 | 30.3 | 2.0 |
| | 51.6 | 49.4 | 78.0 |
| | 73.6 | 71.8 | 23.0 |
| Oxycodone Base | 222.8 | 220.0 | 116.7 |

No peak was observed at the melting point of oxycodone base, demonstrating that no discrete base particles were present in the compositions.

Example 4

Preparation of Drug Containing Microparticles

| Sr. No. | Ingredients | % | Quantity/Batch (g) |
|---|---|---|---|
| 1 | Oxycodone base | 10.00 | 125.00 |
| 2 | Myristic acid | 50.00 | 625.00 |
| 3 | Yellow Beeswax | 20.00 | 250.00 |
| 4 | Carnauba wax | 20.00 | 250.00 |
| | total | 100.00 | 1250.00 |

Procedure:
1. Myristic acid was melted under constant stirring while continuously sparging with nitrogen
2. When Step 1 temperature reaches 70° C., Oxycodone base was added and mixing is continued until a clear molten liquid was fainted.
3. Yellow Beeswax is melted in a separate container. When it reached 70° C., it is added slowly to Step 2 molten liquid and mixed for 5 minutes.
4. Carnauba wax is melted in a separate container. When it reached 90° C., it is added slowly to Step 3 molten liquid and mixed for 5 minutes. A uniform homogeneous mixture was formed.

The molten mixture was solidified and subsequently was milled in a Fitzmill in the presence of dry ice in order to obtain microparticles less than 16 mesh. It is expected that the molten homogeneous mixture formed in step 4 could be spray congealed as an alternative method to form microparticles with a uniform particle size distribution.

Example 5

Preparation of Coated Drug Containing Microparticles

Drug-containing particles formulated in a manner similar to that described in Example 3 were sieved to obtain particles from 20-40 mesh in size. These particles were coated with an insoluble coating comprising Eudragit RS 30D in a fluidized bed apparatus.

Example 6

Preparation of Tablets for Oral Administration

Drug-containing particles formulated in a manner similar to that described in Example 3 were sieved to obtain particles from 20-40 mesh in size. These particles were tableted with the addition of an appropriate amount of filler, disintegrant and lubricant.

Example 7

Preparation of Capsules for Oral Administration

The drug containing microparticles from Example 3 were loaded into gelatin capsules.

It is understood that the disclosed invention is not limited to the particular methodology, protocols, and reagents described as these may vary. Those skilled in the art will recognize, or be able to ascertain using no more than routine experimentation, many equivalents to the specific embodiments of the invention described herein. Such equivalents are intended to be encompassed by the following claims. It is also to be understood that the terminology used herein is for the purpose of describing particular embodiments only. Publications cited herein and the material for which they are cited are specifically incorporated by reference.

We claim:

1. A method for the management of pain comprising administering to a patient in need thereof a therapeutically effective pharmaceutical composition comprising solid microparticles, wherein the microparticles comprise:
   a) an active agent,
   b) one or more fatty acids, and
   c) one or more carrier materials selected from the group consisting of waxes or wax-like substances and mixtures thereof;
wherein the active agent comprises a fatty acid salt of oxycodone, and the one or more fatty acids are present in an amount ranging from 6.9 to 15 times the molar amount of the active agent.

2. The method of claim 1, wherein the molar concentration of the one or more fatty acids in the microparticle is 6.9 to 10 times the molar amount of the active agent.

3. The method of claim 1, wherein the one or more fatty acids is one or more $C_5$ to $C_{30}$ monovalent fatty acids, one or more $C_8$ to $C_{40}$ divalent fatty acids, or mixtures thereof.

4. The method of claim 2 wherein the one or more fatty acids is one or more $C_5$ to $C_{30}$ monovalent fatty acids, one or more $C_8$ to $C_{40}$ divalent fatty acids, or mixtures thereof.

5. The method of claim 3, wherein the one or more fatty acids is one or more $C_5$ to $C_{30}$ monovalent fatty acids selected from the group consisting of pentanoic acid, hexanoic (caproic) acid, heptanoic acid, octanoic (carylic) acid, nonanoic acid, decanoic (capric) acid, undecanoic acid, dodecanoic (lauric) acid, tridecanoic acid, tetradecanoic (myristic) acid, pentadecanoic acid, hexadecanoic (palmitic) acid, heptadecanoic (margaric) acid, octadecanoic (stearic) acid, nonadecanoic acid, eicosanoic (arachidic) acid, heneicosanoic acid, docasanoic (behenic) acid, tricosanoic acid, tetracosanoic (lignoceric) acid, pentacosanoic acid, hexacosanoic acid, heptacosanoic acid, octacosanoic acid, nonacosanoic acid, triacontanoic acid, linoleic acid, oleic acid, and mixtures thereof.

6. The method of claim 4, wherein the one or more fatty acids is one or more $C_5$ to $C_{30}$ monovalent fatty acids selected from the group consisting of pentanoic acid, hexanoic (caproic) acid, heptanoic acid, octanoic (carylic) acid, nonanoic acid, decanoic (capric) acid, undecanoic acid, dodecanoic (lauric) acid, tridecanoic acid, tetradecanoic (myristic) acid, pentadecanoic acid, hexadecanoic (palmitic) acid, heptadecanoic (margaric) acid, octadecanoic (stearic) acid, nonadecanoic acid, eicosanoic (arachidic) acid, heneicosanoic acid, docasanoic (behenic) acid, tricosanoic acid, tetracosanoic (lignoceric) acid, pentacosanoic acid, hexacosanoic acid, heptacosanoic acid, octacosanoic acid, nonacosanoic acid, triacontanoic acid, linoleic acid, oleic acid, and mixtures thereof.

7. The method of claim 5, wherein the one or more fatty acids is myristic acid.

8. The method of claim 6, wherein the one or more fatty acids is myristic acid.

9. The method of claim 1, wherein the one or more carrier materials are present in an amount of from 0.25 to 8 times the weight of the amount of active agent.

10. The method of claim 2, wherein the one or more carrier materials are present in an amount of from 0.25 to 8 times the weight of the amount of active agent.

11. The method of claim 9, wherein the one or more carrier materials are present in an amount of from 2 to 6 times by weight of the amount of active agent.

12. The method of claim 10, wherein the one or more carrier materials are present in an amount of from 2 to 6 times by weight of the amount of active agent.

13. The method of claim 1, wherein the carrier material is a wax selected from the group consisting of carnauba wax, beeswax, microcrystalline wax, and mixtures thereof.

14. The method of claim 2, wherein the carrier material is a wax selected from the group consisting of carnauba wax, beeswax, microcrystalline wax, and mixtures thereof.

15. The method of claim 13, wherein the carrier material is a mixture of beeswax and carnauba wax.

16. The method of claim 14, wherein the carrier material is a mixture of beeswax and carnauba wax.

17. The method of claim 1, wherein the active agent comprises a myristic acid salt of oxycodone, the one or more fatty acids is myristic acid, and the carrier comprises beeswax and carnauba wax.

18. The method of claim 2, wherein the active agent comprises a myristic acid salt of oxycodone, the one or more fatty acids is myristic acid, and the carrier comprises beeswax and carnauba wax.

19. The method of claim 1, wherein the active agent is prepared by contacting a molar excess of one of the one or more fatty acids with the free base form of the active agent.

20. The method of claim 2, wherein the active agent is prepared by contacting a molar excess of one of the one or more fatty acids with the free base form of the active agent.

* * * * *